United States Patent [19]

Knorre et al.

[11] 4,150,244

[45] Apr. 17, 1979

[54] PROCESS FOR THE PRODUCTION OF CRYSTALLINE ALCOHOL FREE ALKALI METAL ALCOHOLATES IN AN INERT SOLVENT

[75] Inventors: Helmut Knorre, Seligenstadt; Manfred Langer, Hanau, both of Fed. Rep. of Germany

[73] Assignee: Deutsche Gold- und Silber-Scheideanstalt vormals Roessler, Frankfurt, Fed. Rep. of Germany

[21] Appl. No.: 779,548

[22] Filed: Mar. 21, 1977

[30] Foreign Application Priority Data

Mar. 25, 1976 [DE] Fed. Rep. of Germany ....... 2612642

[51] Int. Cl.² ............................................. C07C 29/00
[52] U.S. Cl. ................................................... 568/851
[58] Field of Search .................... 260/632 A; 568/851

[56] References Cited

U.S. PATENT DOCUMENTS

| 2,579,257 | 12/1951 | Hansley et al. | 260/632 A |
| 3,971,833 | 7/1976 | Lenz et al. | 260/632 A |

FOREIGN PATENT DOCUMENTS

727923  4/1955  United Kingdom ................ 260/632 A

OTHER PUBLICATIONS

Lange, "Handbook of Chemistry", 10th Ed. (1961), pp. 304–305.

*Primary Examiner*—Joseph E. Evans
*Attorney, Agent, or Firm*—Cushman, Darby & Cushman

[57] ABSTRACT

There is described a process for the production of inert solvent soluble metal alcoholate free from alcohol of crystallization by reacting an alkali metal with an alcohol in an inert solvent above its melting point in an emulsion of the alkali metal in a solvent.

9 Claims, No Drawings

PROCESS FOR THE PRODUCTION OF CRYSTALLINE ALCOHOL FREE ALKALI METAL ALCOHOLATES IN AN INERT SOLVENT

BACKGROUND OF THE INVENTION

The present invention is directed to a new process for the large scale production of alkali metal alcoholates free from alcohol of crystallization which are soluble in inert solvents or mixtures of solvents.

The alkali and alkaline earth metal derivatives of alcohols, phenols and enols are of great significance as intermediates, reactants and catalysts in the synthesis of many organic compounds. A series of different processes are known for their productions (see Houben-Weyl Vol. VI$_2$ (1963) pages 7 et seq.). In principle one of these processes consists of reacting the free alkali metal directly with the alcohol. This reaction takes place more or less vigorously according to the degree of dispersion of the alkali metal. With increasing chain length of the alcohol the reaction is slowed down, primary alcohols reacts most violently, tertiary alcohols the slowest. For example, the reaction speed of tert. butyl alcohol at room temperature is only about 1/65 that of methyl alcohol, that of tert. amyl alcohol only 1/175 (see S. Volpe and G. Tlustos, Annali di Chimica Vol. 62 pages 399–407 (1972).

Precisely the alkali metal derivatives of the last named alcohols, however, in recent times have found increasing interest as catalysts and condensation agents, since both tert. butylate and tert. amylate are particularly strong proton acceptors because of the very small acidity of the pertinent alcohols and the strongly sterically hindered alcohols set free in the reactions for the most part do not undergo side reactions. Since the alkali metal derivatives of the tertiary alcohols in crystal alcohol free form beside are partially well soluble in inert solvents and mixtures of solvents, these alcohols are particularly advantageously added in this form in many reactions.

For the production of alkali metal alcoholates free from alcohol of crystallization therefore for a long time there has been sought a simple large scale process. Mainly, the previously proposed processes are suited almost exclusively for preparations on a laboratory scale, be it because the products are produced with excess alcohol and thus must be freed from alcohol of crystallization by a time consuming and cumbersome operation or be it because the alcohols must be reacted with expensive and difficult to handle reagents such as sodium hydride or sodium amide (see Houben-Weyl, Vol. VI$_2$ (1963) pages 11 et seq.).

Also the process of Lochmann, Coupen and Lim (see *Collection Czechosl. Chem. Comm.* Vol. 35 pages 733–736 (1970)) in which alkali derivatives are first separated as adducts of tetrahydrofuran and are obtained from these adducts in pure form by evaporation of the tetrahydrofuran is too cumbersome for the production of the alcoholates on a commercial scale.

For the direct production of alkali metal alcoholates of tertiary alcohols free from alcohol of crystallization in inert solvents or solvent mixtures there has recently been proposed a process in which the added metal is used in equimolar amounts or preferably in excess and in which the reaction is carried out in an inert solvent or solvent mixture under increased pressure at temperatures at which or above which the alcohol of crystallization is split off (see German Auslegeschrift No. 2,333,634). In this process, however, there are still needed undesirably long reaction times. Also, disadvantageous are the high reaction temperatures as well as the alkali metal excess required in this process which in the course of several reactions is enriched with impurities which lead to disturbances or to expensive purification operations.

It is also known to increase the reaction speed in the reaction of long chain primary alcohols by adding the alkali metal in a finely "atomized" condition. According to the previously described processes, however, there can be produced alkali metal derivatives of unbranched primary alcohols free from alcohol of crystallization if first there is formed an alkali metal dispersion in boiling hydrocarbons and after cooling this there is dropped in the calculated amount of the primary alcohol (see Houben-Weyl, Vol. VI$_2$ (1963) page 8; Ethyl, British Pat. No. 727,923). However, according to this proposal it is not possible to employ secondary and tertiary alcohols as well as iso-alcohols and those with a branched chain in rapid reaction. The reactivity of the last named alcohols with alkali metals is so small that according to the known process industrially unusable long reaction times are required. If one tries to carry out the described process then in an expensive manner one must first produce a sodium dispersion in xylene in 30 minutes, which dispersion is added for this reaction only after cooling. However, even with a dispersion of 5$\mu$ particle size in reacting tertiary alcohols at room temperature no satisfactory reaction speeds are developed so that even at the sought reaction times of up to 30 minutes the added alcohol after a few minutes no longer reacts completely; the remaining unreacted alcohol then leads to the precipitation of alcohol of crystallization containing alcoholates. An increase of the reaction temperature up to the melting point of sodium likewise does not lead to the desired results because with increasing temperature the sodium metal increasingly softens and therefore with the still necessary reaction times of over 15 minutes the dispersion clots together after a few minutes.

Therefore, there must be tried other ways to produce the desired alcohol of crystallization free alkali metal alcoholates in an economical industrial process. The object of the present invention therefore was to develop a process for the production of these alcoholates soluble in inert solvents which does not have the described disadvantages, i.e., without excess of a reactant in economically usable reaction times and in a simple reaction of alkali metal with alcohol in an inert solvent or solvent mixture form the desired, previously difficult producible alcoholates.

SUMMARY OF THE INVENTION

The object of the invention is the development of a process for the production of inert solvent soluble, alcohol of crystallization free, alkali metal alcoholates by reaction of alkali metals with alcohols in an inert solvent or mixture of solvents. The process consists of reacting the alcohol at temperatures above the melting point of the alkali metal in an emulsion of the same in a solvent or mixture of solvents.

An advantageous form consists of dispersing the alkali metal at a temperature above its melting point, in a given case under superatmospheric pressure, in the solvent or mixture of solvents in a reactor and simultaneously or afterwards adding the stoichiometric amount of reacting alcohol under continued dispersing.

Another very simple and reliable method consists of dispersing the alkali metal in the solvent or mixture of solvents heated to a temperature above the melting point of the alkali metal, in a given case under superatmospheric pressure, the solvent containing the stoichiometric amount of the alcohol to be reacted.

During the reaction the dispersing aggregate is always held in operation and the temperature is above the melting point of the alkali metal.

In this manner the disadvantages of the previously described processes can be avoided because at temperatures above the melting point of the alkali metal the alkali metal is continuously dispersed again during the reaction so that there is offered to the alcohol up to the end of the reaction a steadily renewed, very large and fresh alkali metal surface. Thereby even at temperatures barely above the melting point of the alkali metal reaction speeds are attained which make possible a throughput for the reactor which is satisfactory for large scale purposes and economical.

Simultaneously it is guaranteed that even at high dosing speeds of alcohol addition up to the end of the reaction sufficient alkali metal surface capable of reaction is exposed to the alcohol. Thereby the formation of alcoholates of crystallization is safely excluded if the reaction is carried out below the temperature at which the alcohol of crystallization of the concerned alcoholate is split off.

The process of the invention operates without an excess of alkali metal, whereby the working up of the excess alkali which is undesired in industrial operation and is accompanied by risks is eliminated. A further advantage is the relatively low reaction temperature whereby operation can be carried out at lower pressure and whereby further undesired side reactions are avoided.

The process of the invention is particularly advantageously carried out if during the reaction a fine degree of subdivision of the alkali metal is attained which corresponds to a particle size of at most $100\mu$, preferably at most $30\mu$. As reaction medium there can be used all inert solvents which do not react with the alkali metal, alcohol or alcoholate, as, for example, aliphatic hydrocarbons, aromatic, aliphatic substituted aromatic and cycloaliphatic hydrocarbons, particularly pentane, hexane, heptane, octane, cyclohexane, benzene, toluene, xylene, ethylbenzene, petroleum ether, ligroin, paraffin oils, etc., as well as mixtures of such solvents with each other. Additional solvents include 1,3,5-triethyl benzene, mesitylene, cumene, cymene, decane decalin, decane, dodecane.

The preferred alkali metal is sodium. However, there can also be used potassium or lithium for example.

The invention is particularly suitable for the production of alcoholates of secondary alcohols, tertiary alcohols and branched chain alcohols with more than three carbon atoms. Examples of such alcohols are tert. butyl alcohol, tert. amyl alcohol, sec. butyl alcohol, sec. amyl alcohol, isooctyl alcohol, 2-ethylhexyl alcohol, pentanol-2, octanol-2, tert. octyl alcohol, isodecyl alcohol, isohexadecyl alcohol. The process can also be used with advantage in the production of alkali metal derivatives of straight chain primary alcohols, especially high molecular weight alcohols, e.g., with 8 or more carbon atoms, n-octyl alcohol, n-decyl alcohol, lauryl alcohol, myristyl alcohol, cetyl alcohol, stearyl alcohol. Lower alcohols include n-butyl alcohol, n-hexyl alcohol, ethyl alcohol, methyl alcohol. With the higher straight chain primary alcohols, however, because of their insolubility the corresponding alcoholate suspensions themselves are obtained in solvent or mixture of solvents used.

The process can comprise, consist essentially of or consist of the steps set forth with the materials shown.

The process of the invention will be further explained in connection with the Examples.

DESCRIPTION OF THE PREFERRED EMBODIMENTS

EXAMPLE 1

In a 5-liter reactor resistant to pressure up to 11 atmospheres absolute which is equipped with dispersing apparatus, heat exchanger (as a reflux condenser) and metering pump there were placed 3.5 kg of a solvent mixture of toluene and cyclohexane in the weight ratio of 1:10 as well as 92 grams (4.0 mols) of clean sodium-metal. After heating the mixture to 140° C., the dispersing apparatus was switched on; then there were dosed into the reactor within 8 minutes 296.5 grams (4.0 mols) of dry tert. butanol.

The hydrogen formed in the reaction escaped over a pneumatically controlled pressure maintaining apparatus which previously was adjusted to 4.5 atmospheres absolute. During the reaction the temperature in the reactor remained at 140° C. The heat of reaction as well as the excess energy of the dispersing apparatus were drawn off at the reflux condenser through the solvent mixture refluxing at 130° C.

Immediately after the end of the alcohol addition the reaction mixture was released from pressure and drawn off. There was obtained a yellow colored, clear solution of sodium tert. butylate. The reaction was complete.

EXAMPLE 2

In the previously described reactor there were heated 3.5 kg of the solvent mixture according to example 1 to 150° C. whereupon the pressure adjusted itself to 6 – 6.5 atmospheres absolute. Then the dispersing apparatus was switched on and there were fed in uninterruptedly with a pump exactly 92 grams (4.0 mols) of liquid sodium metal.

Then there were fed in within 15 minutes 352.5 grams (4.0 mols) of dry tert. amyl alcohol. The reaction was then controlled as in Example 1.

One minute after the end of the alcohol addition the reaction mixtures were relieved of pressure and drawn off. There was obtained a yellow colored clear solution of sodium tert. amylate. The reaction was complete.

EXAMPLE 3

3.5 kg of a solvent mixture of 90% cyclohexane and 10% toluene and 296.5 grams (4.0 mols) of tert. butanol were heated to 150° C. in the above-described reactor. Then the dispersing apparatus was switched on and thereupon there was quickly fed in 92 grams (4.0 mols) of liquid sodium.

After a reaction time of 20 minutes wherein the temperature was held at 150° C. at a pressure of 6 – 6.5 atmospheres absolute and the hydrogen formed escaped over a pneumatically controlled pressure maintaining apparatus, the mixture was released from pressure and drawn off. There was obtained a clear, colorless solution of sodium tert. butylate. The reaction was complete.

EXAMPLE 4 (Comparison Example)

There were present in a 2-liter four necked flask equipped with a fine metering funnel, anchor agitator, feedpipe and internal thermometer 23 grams (1.0 mol) of sodium dispersed to a size of $5\mu$ in 800 ml of a solvent mixture of 1 part by weight toluene and 10 parts by weight cyclohexane. There were dropped into this mixture with moderate stirring under nitrogen within 30 minutes 74.1 grams (1.0 mol) of dry tert. butanol.

Already after the addition of a small amount of alcohol the reaction mixture was difficult to stir because of the gel-like precipitating alcoholate of crystallization. After the ending of the addition of alcohol less than half of the sodium had reacted. The excess sodium dispersion still present in the gel-like solidified reaction mixture only reacted completely after standing for several hours.

EXAMPLE 5 (Comparison Example)

The reaction was carried out as in Example 4 but in order to accelerate the reaction, the temperature was increased to 80° C. With a time of dropping in alcohol of 30 minutes clumping together of the sodium dispersion was observed at the latest after 10 minutes. Simultaneously because of the now strongly retarded reaction there separated out gel-like, insoluble alcoholate of crystallization and the reaction medium thickened. The reaction only ran to at most 20%.

What is claimed is:

1. A process for the production of inert solvent soluble alkali metal alcoholate free from alcohol of crystallization consisting essentially of reacting an emulsion of sodium or potassium in an inert solvent with tert, butanol or tert, amyl alcohol at a temperature which is above the melting point of the alkali metal and below the temperature at which the alcoholate of crystallization splits out alcohol of crystallization.

2. The process of claim 1 wherein the alkali metal is sodium.

3. The process of claim 1 wherein the inert solvent is a hydrocarbon solvent.

4. The process of claim 3 wherein the solvent is a single hydrocarbon.

5. The process of claim 3 wherein the solvent is a mixture of hydrocarbons.

6. The process of claim 1 wherein the alkali metal is dispersed to a particle size below $100\mu$.

7. The process of claim 6 wherein the alkali metal is dispersed to a particle size below $30\mu$.

8. The process of claim 1 comprising dispersing the alkali metal in the inert solvent above the melting point of the alkali metal and adding the stoichiometric amount of tert, butanol or tert, amyl alcohol to said dispersed alkali metal while continuously dispersing said alkali metal.

9. The process of claim 1 comprising dispersing the alkali metal in a solution of the stoichiometric amount of tert, butanol or tert, amyl alcohol in an inert solvent at a temperature above the melting point of the alkali metal.

* * * * *